United States Patent [19]

Martineau

[11] Patent Number: 5,647,835
[45] Date of Patent: Jul. 15, 1997

[54] METHOD FOR PREVENTING MOTION SICKNESS

[76] Inventor: Michael Martineau, 15 Beachhill Rd., West Granville, Mass. 01034

[21] Appl. No.: 493,667

[22] Filed: Jun. 22, 1995

[51] Int. Cl.⁶ .................................................. A61M 21/00
[52] U.S. Cl. .................................................. 600/27; 128/898
[58] Field of Search ............... 600/26–27; 128/897–98; 2/12, 13, 15, 431–433; 351/46

[56] References Cited

U.S. PATENT DOCUMENTS

| | | |
|---|---|---|
| 1,532,480 | 4/1925 | Finch . |
| 2,107,102 | 12/1938 | Catron, Jr. . |
| 2,211,366 | 6/1940 | Cooper .................................. 2/12 |
| 2,433,590 | 12/1947 | Barr ..................................... 2/13 |
| 3,212,102 | 10/1965 | Muller .................................. 2/12 |
| 3,523,375 | 8/1970 | Frith et al. ........................... 2/432 |
| 4,298,991 | 11/1981 | Recenello ............................ 2/13 |
| 4,751,746 | 6/1988 | Rustin ................................... 2/13 |
| 4,929,228 | 5/1990 | Hendricks ............................ 600/27 |
| 4,981,146 | 1/1991 | Bertolucci ........................... 128/802 |
| 5,067,941 | 11/1991 | Hendricks ............................ 600/27 |
| 5,146,623 | 9/1992 | Payson et al. ....................... 2/12 |
| 5,224,495 | 7/1993 | Robinson ............................. 128/857 |

*Primary Examiner*—John P. Lacyk
*Attorney, Agent, or Firm*—White & Case

[57] ABSTRACT

An apparatus and method for preventing motion sickness are provided. The apparatus comprises a blinder attached to a support and positioned for confining the vision of a person susceptible to motion sickness to block all visual information indicative of motion.

6 Claims, 1 Drawing Sheet

METHOD FOR PREVENTING MOTION SICKNESS

BACKGROUND OF THE INVENTION

1. Field of the Invention

The invention relates generally to an apparatus and method for preventing motion sickness. The invention relates in particular to an apparatus and method for preventing motion sickness while reading in a moving vehicle by physically blocking out visual information indicative of motion.

2. Description of the Prior Art

Presently, a number of different drugs are offered for preventing motion sickness associated with travelling in a vehicle, such as a car, boat or plane. The available drugs, however, have undesirable side effects, which can be particularly hazardous if the person sensing the side effects is also operating the vehicle. In addition, drugs are inconvenient because they must be taken just prior to travel. A number of other disadvantages related to such drugs are well known.

A few products have been offered to prevent motion sickness without the use of drugs. For instance, U.S. Pat. Nos. 5,067,941 and 4,939,228 disclose an anti-motion sickness apparatus. These patents focus on alleviating motion sickness attributable to the mismatch between the motion experienced by fluid in the inner ear of the person and the vision of the person. This mismatch is caused when fluid in the inner ear senses motion, while the eyes fail to sense such motion visually. The apparatus disclosed in these patents provides a visually discernible wave motion image, such as moving liquid, which visually confirms the motion in the inner ear. This avoids the mismatch and thus prevents the motion sickness associated with it.

Another cause of motion sickness relates to the input of information to the brain stem which is interpreted as a spin. For example, when a person travelling in a moving vehicle looks forward, as one would while driving an automobile, the brain receives sufficient information to know that it is moving forward and not spinning around. However, when the eyes are focused on something inside the vehicle, such as a book, the input from peripheral vision, such as that associated with the passing of trees and telephone poles and shadows therefrom, gives the sensation of a spin, so real, that it produces a literal nystagmus (the phenomenon induced when a person is spun, wherein the eyes move back and forth in rhythmic pulses) as well as the concomitant motion sickness associated with spinning.

It would therefore be desirable to have an apparatus which prevents motion sickness associated with the visual reception of peripheral information interpreted by the brain as spinning.

SUMMARY OF THE INVENTION

The invention provides an apparatus and method for preventing motion sickness in a person susceptible thereto. The apparatus comprises a support having means for securing the apparatus to the head of the person and a blinder attached to the support. The blinder has portions positioned to at least either side and above the eyes of the person when the support is secured to the person's head. These portions of the blinder confine the vision of the person to block out any peripheral visual information indicative of motion.

The method of the invention comprises confining the vision of the person to block out any peripheral visual information indicative of motion.

DETAILED DESCRIPTION OF THE PREFERRED EMBODIMENT

Figure 1:
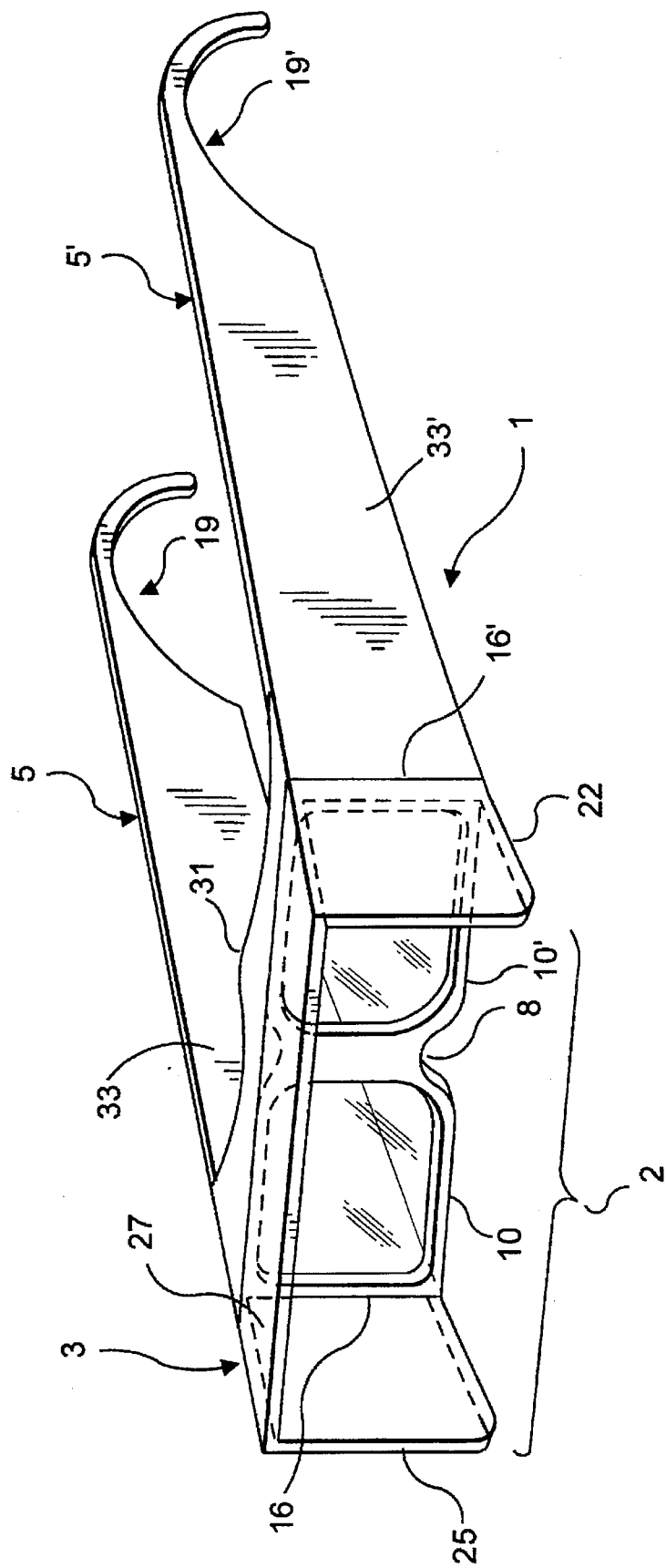
FIG. 1 is a perspective view of one embodiment of the invention.

FIG. 1 shows an apparatus of the present invention. In the preferred embodiment, the apparatus comprises a support 1 including frame 2 and means for securing the apparatus to the head of a person (not shown), such as articulating arms 5 and 5'. A blinder 3 is also attached to frame 2.

Frame 2 has a longitudinally centered nose-bridge 8 for supporting the apparatus on the nose of the person (also not shown). Frame 2 also has sections 10 and 10' to each side of the nose-bridge 8 which extend to opposed ends 16 and 16' beyond the temples of the person when the apparatus is secured to the head of the person. Articulating arms 5 and 5' are attached to the opposed ends 16 and 16', respectively, and have distal portions 19 and 19' which are shaped to fit over the ears of the person (not shown) when they are unfolded from nose-bridge 8. In this manner, the apparatus may be secured to the person. Articulating arms 5 and 5' also have enlarged opaque portions 33 and 33' proximate to opposed 16 and 16' ends which aid blinder 3 to block the peripheral vision of the person.

The blinder 3 preferably comprises three opaque view blocking panels 22, 25 and 27 positioned on frame 2 and protruding therefrom to block the respective left, right and upward peripheral views of the person. Upper view blocking panel 27 has a curved inner edge 31 shaped to contour the brow of the person when the apparatus is worn. Thus, when support 1 is secured to the head of the person and the person looks down at an object inside a moving vehicle, such as a book inside a car, view blocking panels 22, 25 and 27 and enlarged portions 33 and 33' will prevent the person from seeing any external visual information indicative of motion, such as objects or shadows passing outside the car. This prevents the nystagmus and associated motion sickness which would otherwise occur.

The method of the present invention comprises confining the vision of a person susceptible to motion sickness to block out any peripheral visual information indicative of motion. Specifically, for a person travelling in a vehicle, the method comprises blocking the left, right and upward peripheral views as the person looks down at an object in the vehicle in order to block out any external visual information indicative of motion, such as passing objects or shadows outside the vehicle.

What is claimed is:

1. A method for preventing motion sickness comprising:
    confining the vision of a person susceptible to motion sickness to block out any peripheral visual information indicative of motion.

2. The method according to claim 1, further comprising confining the vision of a person travelling in a vehicle by blocking the left, right and upward peripheral views as the person looks down at an object in the vehicle.

3. The method according to claim 2, further comprising:
    providing an apparatus for confining the vision of the person; and
    securing the apparatus to the head of the person.

4. The method according to claim 3, further comprising:

providing as the apparatus a support having means for securing the apparatus to the head of the person, and blinder means attached to the support and having portions positioned at least to either side and above the eyes of the person when the support is secured to the head of the person.

5. The method according to claim 4, further comprising:

providing as the support a frame having a longitudinally centered nose-bridge for supporting the frame on the nose of the person; sections attached to each side of the nose-bridge and extending to opposed ends; and articulating arms attached to the opposed ends, said arms having distal portions shaped for fitting over the ears of the person when unfolded from the nose-bridge.

6. The method of claim 5, further comprising providing opaque panels as the blinder means.

* * * * *